United States Patent
Nissl

(10) Patent No.: US 8,323,350 B2
(45) Date of Patent: Dec. 4, 2012

(54) DUODENUM STENT AND ASSOCIATED METHOD

(75) Inventor: Thomas Nissl, Winsen / Luhe (DE)

(73) Assignee: Merit Medical Systems, Inc., South Jordan, UT (US)

( * ) Notice: Subject to any disclaimer, the term of this patent is extended or adjusted under 35 U.S.C. 154(b) by 440 days.

(21) Appl. No.: 11/400,630

(22) Filed: Apr. 7, 2006

(65) Prior Publication Data

US 2006/0259051 A1 Nov. 16, 2006

Related U.S. Application Data

(60) Provisional application No. 60/702,826, filed on Jul. 27, 2005.

(30) Foreign Application Priority Data

Apr. 8, 2005 (DE) .......................... 10 2005 016 103

(51) Int. Cl.
*A61F 2/04* (2006.01)
*A61F 2/06* (2006.01)

(52) U.S. Cl. ...................... 623/23.7; 623/1.15; 623/1.22; 623/1.31; 623/1.37

(58) Field of Classification Search .................. 623/1.22, 623/1.15–1.21, 1.3–1.31, 1.37, 23.64–23.7; 604/8
See application file for complete search history.

(56) References Cited

U.S. PATENT DOCUMENTS

| | | | |
|---|---|---|---|
| 3,044,497 A | 7/1962 | Rebut | |
| 5,129,910 A | 7/1992 | Phan et al. | |
| 5,330,500 A | 7/1994 | Song | |
| 5,514,176 A | * 5/1996 | Bosley, Jr. | 623/1.15 |
| 5,824,054 A | * 10/1998 | Khosravi et al. | 623/1.44 |
| 5,876,448 A | 3/1999 | Thompson et al. | |
| 6,017,365 A | 1/2000 | Von Oepen | |
| 6,106,548 A | 8/2000 | Roubin et al. | |
| 6,146,416 A | * 11/2000 | Andersen et al. | 623/1.15 |
| 6,176,873 B1 | 1/2001 | Ouchi | |
| 6,224,626 B1 | 5/2001 | Steinke | |

(Continued)

FOREIGN PATENT DOCUMENTS

DE 297 08 879 U1 7/1997

(Continued)

OTHER PUBLICATIONS

WALLSTENT® Endoprosthesis, *Boston Scientific*; 11 pages, available at http://www.bostonscientific.com/med_specialty/deviceDetail.jhtml?task=tskBasicDevice.jht . . . .

(Continued)

*Primary Examiner* — David Isabella
*Assistant Examiner* — Andrew Iwamaye
(74) *Attorney, Agent, or Firm* — Stoel Rives LLP

(57) ABSTRACT

A stent for positioning within a lumen is provided. The stent includes a stent region and a pair of transition regions extending from respective ends of the stent region, wherein each of the transition and stent regions define an aperture therethrough. At least a portion of at least one of the transition regions is configured in a helix including a plurality of turns, wherein the stent region is capable of expanding to conform to a stricture and each of the transition regions is capable of expanding to conform to the lumen proximally and distally of the stricture.

40 Claims, 4 Drawing Sheets

U.S. PATENT DOCUMENTS

| | | | |
|---|---|---|---|
| 6,241,757 B1 * | 6/2001 | An et al. ........................ | 623/1.1 |
| 6,248,058 B1 | 6/2001 | Silverman et al. | |
| 6,302,917 B1 | 10/2001 | Dua et al. | |
| 6,325,825 B1 * | 12/2001 | Kula et al. ........................ | 623/1.3 |
| 6,338,739 B1 * | 1/2002 | Datta et al. .................. | 623/1.15 |
| 6,379,379 B1 * | 4/2002 | Wang ............................ | 623/1.15 |
| 6,416,545 B1 | 7/2002 | Mikus et al. | |
| 6,425,915 B1 * | 7/2002 | Khosravi et al. .............. | 623/1.22 |
| 6,475,232 B1 | 11/2002 | Babbs et al. | |
| 6,494,889 B1 * | 12/2002 | Fleischman et al. .......... | 606/155 |
| 6,494,908 B1 | 12/2002 | Huxel et al. | |
| 6,505,654 B1 | 1/2003 | Andersen et al. | |
| 6,589,213 B2 | 7/2003 | Reydel | |
| 6,652,573 B2 | 11/2003 | von Oepen | |
| 6,675,809 B2 | 1/2004 | Stack et al. | |
| 6,746,489 B2 | 6/2004 | Dua et al. | |
| 6,818,015 B2 | 11/2004 | Hankh et al. | |
| 6,899,730 B1 * | 5/2005 | Rivelli, Jr. .................... | 623/1.15 |
| 2002/0007222 A1 * | 1/2002 | Desai .......................... | 623/23.65 |
| 2002/0077693 A1 * | 6/2002 | Barclay et al. ................ | 623/1.13 |
| 2003/0014127 A1 * | 1/2003 | Talja et al. .................. | 623/23.75 |
| 2003/0040803 A1 | 2/2003 | Rioux | |
| 2003/0040804 A1 * | 2/2003 | Stack et al. .................. | 623/23.7 |
| 2003/0130611 A1 | 7/2003 | Martin | |
| 2003/0195609 A1 * | 10/2003 | Berenstein et al. .......... | 623/1.15 |
| 2003/0212450 A1 | 11/2003 | Schlick | |
| 2004/0034408 A1 * | 2/2004 | Majercak et al. ............ | 623/1.15 |
| 2004/0098105 A1 * | 5/2004 | Stinson et al. ................ | 623/1.15 |
| 2004/0122504 A1 * | 6/2004 | Hogendijk .................... | 623/1.15 |
| 2004/0193283 A1 | 9/2004 | Rioux et al. | |
| 2005/0010275 A1 | 1/2005 | Sahatjian et al. | |
| 2005/0075715 A1 | 4/2005 | Borges et al. | |
| 2005/0143805 A1 | 6/2005 | Hierlemann et al. | |
| 2005/0171556 A1 * | 8/2005 | Murphy ........................ | 606/108 |
| 2006/0184238 A1 * | 8/2006 | Kaufmann et al. .......... | 623/1.53 |

FOREIGN PATENT DOCUMENTS

| | | |
|---|---|---|
| DE | 691 26 428 T2 | 10/1997 |
| DE | 197 54 747 A1 | 6/1999 |
| DE | 199 49 334 A1 | 5/2001 |
| DE | 693 33 161 T2 | 6/2004 |
| FR | 1103165 | 10/1955 |
| GB | 2 069 339 A | 8/1981 |
| JP | 2002-233580 | 8/2002 |
| WO | WO-90/04982 A1 | 5/1990 |
| WO | WO-94/12136 A1 | 6/1994 |
| WO | WO-96/41589 A1 | 12/1996 |
| WO | WO-99/49810 A1 | 10/1999 |
| WO | WO-01/58384 A1 | 8/2001 |
| WO | WO 01/72239 | 10/2001 |
| WO | WO 01/72239 A2 * | 10/2001 |
| WO | WO-01/89419 A1 | 11/2001 |
| WO | WO-02/069848 A2 | 9/2002 |
| WO | WO-2004/096097 A2 | 11/2004 |
| WO | WO 2005/011527 | 2/2005 |

OTHER PUBLICATIONS

Polyflex® Esophageal Stent, *Boston Scientific*, 4 pages, available at http://www.bostonscientific.com.med_specialty/deviceDetail.jhtml?task=tskBasicDevice.jht . . . .

Roy L. Gordon, M.D.; *Percutaneous Biliary Drainage and Stenting*, 16 pages, 1995.

PCT Notification of Transmittal of the International Search Report and the Written Opinion of the International Searching Authority, or the Declaration, mailed Aug. 22, 2006 for PCT/US2006/013129 (Filed Apr. 6, 2006).

Ultraflex™ Esophageal NG Stent System, *Boston Scientific*; 2 pages, available at http://www.bostonscientific.com/med_specialty/deviceDetail.jsp?task=tskBasicDevice.jsp; Downloaded on May 19, 2005.

Polyflex® Esophageal Stent, *Boston Scientific*, 2 pages, available at http://www.bostonscientific.com/med_specialty/deviceDetail.jhtml?task=tskBasicDevice.jht; Downloaded on May 19, 2005.

* cited by examiner

DUODENUM STENT AND ASSOCIATED METHOD

CROSS-REFERENCE TO RELATED APPLICATIONS

The present application claims priority from German Application No. DE 10 2005 016 103, entitled "Duodenum Stent," filed Apr. 8, 2005, and U.S. Provisional Application No. 60/702,826 entitled "Duodenum Stent and Associated Method," filed Jul. 27, 2005, the contents of which are incorporated herein by reference.

BACKGROUND OF THE INVENTION

1) Field of the Invention

The present invention relates to a stent device and, in more particular, to a stent device that is capable of being positioned within a lumen.

2) Description of Related Art

Stents are devices that are inserted into body lumens such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus for strictures or cancer. Vascular as well as nonvascular stenting has evolved significantly; unfortunately, there remain significant limitations with respect to the effectiveness of the stents following implantation into a patient's duodenum.

Stenting of the duodenum has proven to be challenging. The duodenum is a generally C-shaped portion of the small intestine that extends between the stomach and the jejunum. The duodenum is subject to complications that may require stenting, surgical repair, or balloon dilatation. For example, a defective portion of the duodenum such as a benign or malignant tumor is typically surgically removed, and the two cut ends are brought together and reattached. Months or years later a stricture may develop within the lumen of the duodenum either from the buildup of fibrous tissue proximate to the repaired lumen or from the growth of a malignant tumor, each necessitating stenting or further surgical repair to prevent the lumen from constricting further.

Conventional stents utilized for the duodenum have significant drawbacks. Because the duodenum is very soft and flexible compared to other lumens, preventing migration of the stent is problematic. In particular, the duodenum frequently changes size and position, which causes complications for typical stents. For instance, a stent having a constant diameter along its entire axial length will have a tendency to migrate as the duodenum expands. The stricture is narrower than the lumen located proximally and distally of the stricture, and the stent is longer than the length of the stricture such that the portion of the stent proximate to the stricture does not help prevent the stent from migrating. Therefore, there is an increased possibility that the stent will migrate or even turn sideways within the lumen. Moreover, the duodenum is very soft and flexible compared to other lumens, which presents design challenges. For example, the duodenum could fold over itself and slide into the openings of the stent, effectively occluding the stent.

Thus, there is a need in the industry for a duodenum stent that is capable of conforming to a lumen and maintaining the opening through a stricture. In addition, there is a need for a duodenum stent that reduces migration and the possibility of obstruction of the stent openings.

BRIEF SUMMARY OF THE INVENTION

The invention addresses the above needs and achieves other advantages by providing a stent for a lumen. The stent includes a stent region and a pair of transition regions positioned on the proximal and distal ends of the stent region. Each of the transition regions is generally more flexible than the stent region and has a larger diameter than at least a portion of the stent region. With this configuration, the stent region may be positioned proximate to a stricture, while the transition regions are positioned proximally and distally of the stricture. As a result, the stent is capable of not only maintaining or even expanding the stricture but also mimicking the size and movement of the lumen proximal and distal of the stricture to decrease the incidence of migration.

In one embodiment of the present invention, a flexible stent for positioning within a body lumen is provided. The stent includes a stent region having proximal and distal ends and an aperture defined therethrough, wherein the stent region could include scaffolding. The stent also includes a first transition region extending outwardly from an end of the stent, and at least a portion of the first transition region is configured in a helix including a plurality of turns. The first transition region has a larger diameter than at least a portion of the stent region and has an aperture defined therethrough. The stent further includes a second transition region extending outwardly from an opposite end of the stent, wherein the second transition region has a larger diameter than at least a portion of the stent region and has an aperture defined therethrough. The first transition region could be longer than the second transition region, and the proximal and distal ends of the stent region could flare outwardly from a medial portion of the stent region such that a diameter of each of the first and second transition members is larger than the medial portion. Each of the apertures of the first and second transition regions and stent region are substantially collinear, and each of the first and second transition regions are capable of expanding from a first diameter prior to being deployed into the lumen to a larger second diameter after being deployed into the lumen. The stent region may also be capable of expanding after deployment to further engage the stricture.

In various aspects of the stent, each of the turns of the helix includes a different width and/or a substantially rectangular cross section. The helix could include a plurality of turns and/or define a gap between each of the turns. The stent may further include a plurality of connectors, wherein each connector extends across each gap and between respective turns of the helix. Each of the turns of the helix may increase in diameter as the turns extend further away from the stent region. Moreover, the second transition region could be configured in a helix comprising a plurality of turns.

In additional aspects of the stent, the second transition region includes a plurality of leg members extending axially from an end of the stent region. Each of the leg members may be separated by a gap and may be substantially rectangular in cross section. The leg members could be substantially parallel to one another and to each of the apertures of the first and second transition regions and stent region, or the leg members could angle outwardly from the distal end of the stent region. The second transition region may further include a helix extending from at least one of the leg members. Additionally, each of the leg members could be a different length and/or configured to define an angled opening.

In another embodiment of the present invention, each of the transition regions may be formed from a more flexible material then the stent region and/or may be larger in diameter than at least a portion of the stent region. At least a portion of at least one of the transition regions is configured in a helix including a plurality of turns, wherein the stent region is capable of maintaining the patency of a stricture and each of the transition regions is capable of expanding to conform to the lumen proximally and distally of the stricture.

Furthermore, one aspect of the present invention provides a method for deploying a stent within a body lumen. The method includes providing a stent having a stent region and a pair of transition regions extending from respective ends of the stent region. At least a portion of at least one of the transition regions is configured in a helix including a plurality of turns. The method also includes contracting the stent to a diameter smaller than that of the lumen and positioning the stent in a predetermined position within the lumen. The method further includes deploying the stent within the lumen such that stent region maintains the patency of a stricture and each of the transition regions expands to conform to the lumen proximally and distally of the stricture.

In aspects of the method, the providing step includes providing a pair of transition regions each configured in a helix comprising a plurality of turns. In addition, the providing step could include providing a transition region having a plurality of leg members extending axially from the stent region. The positioning step may include positioning the stent within the lumen with an endoscope.

BRIEF DESCRIPTION OF THE SEVERAL VIEWS OF THE DRAWINGS

Figure 1:
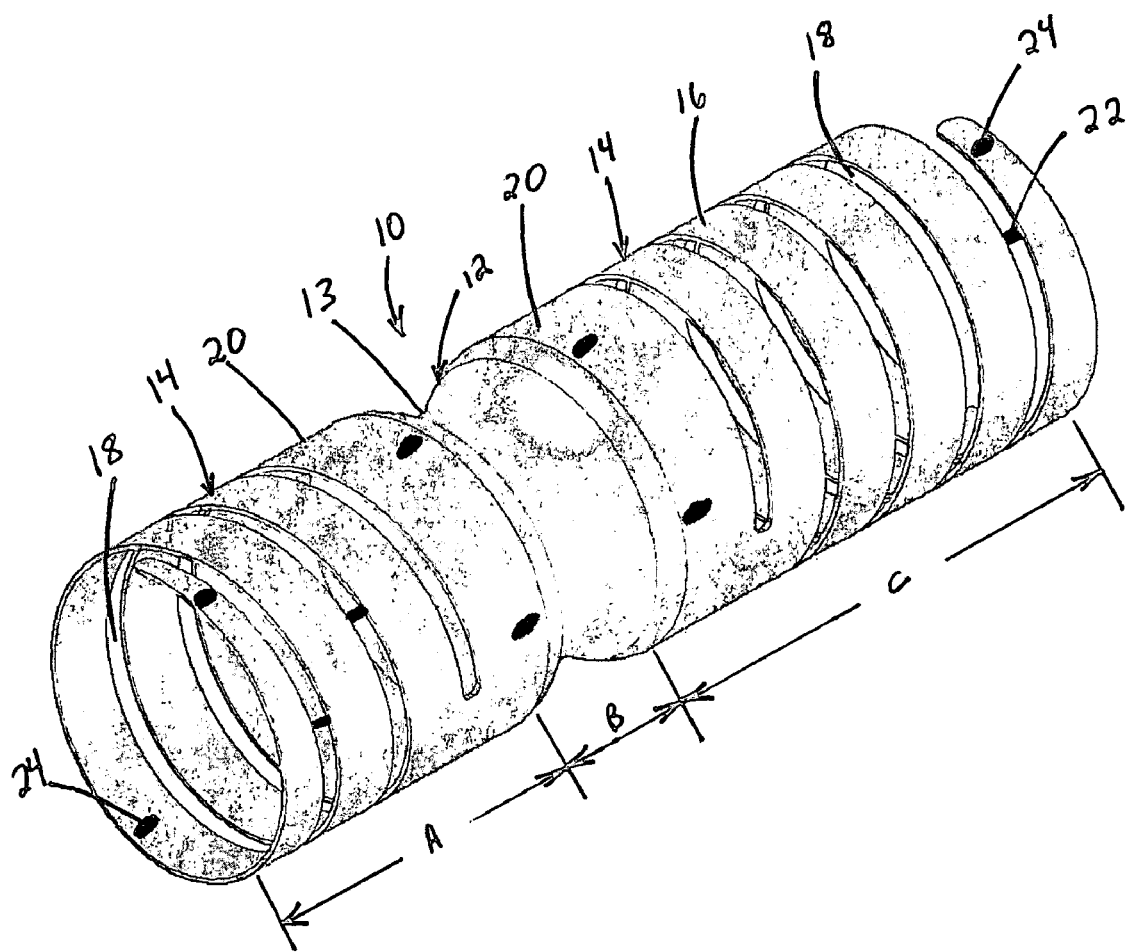
Figure 2:
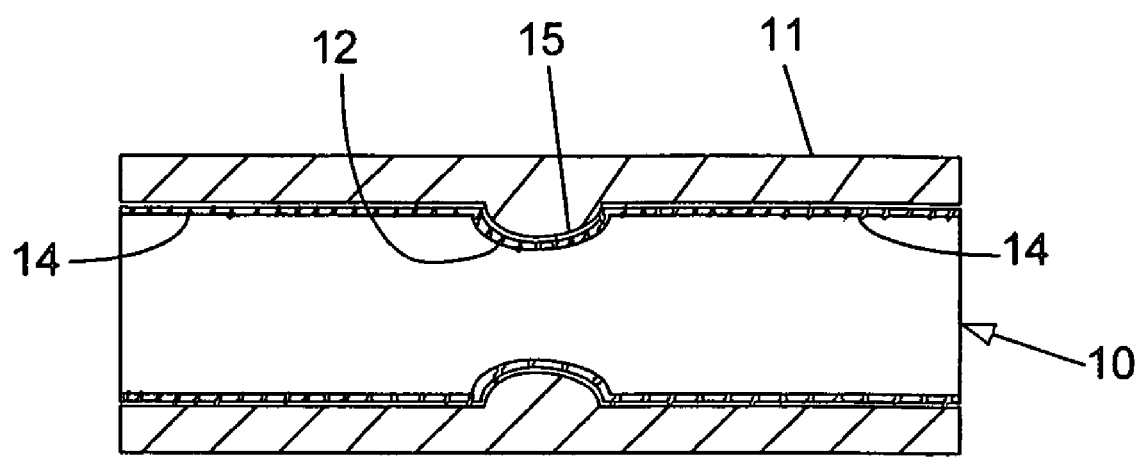
Figure 3:
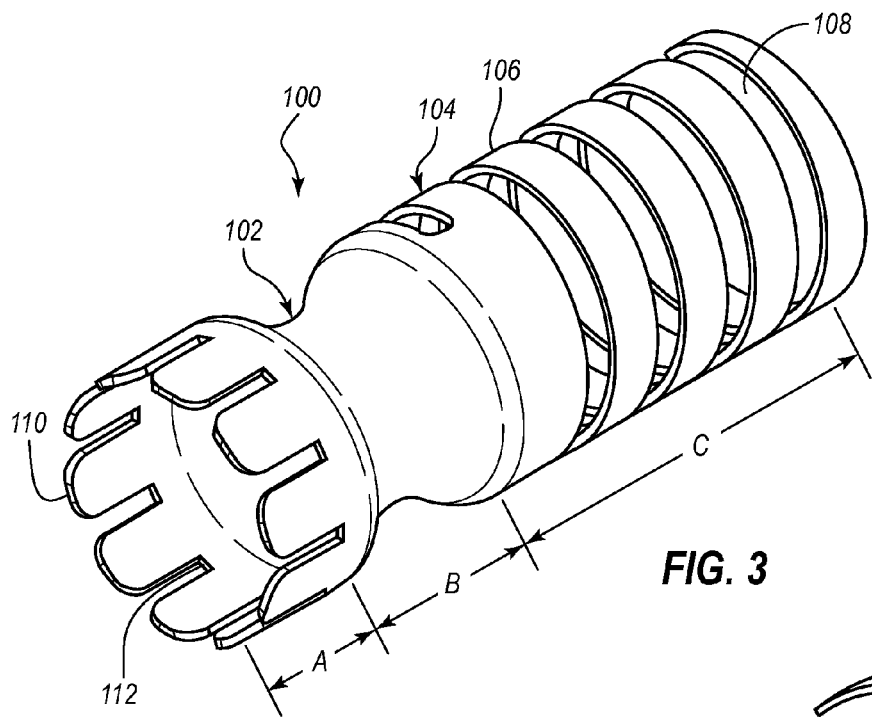
Figure 3A:
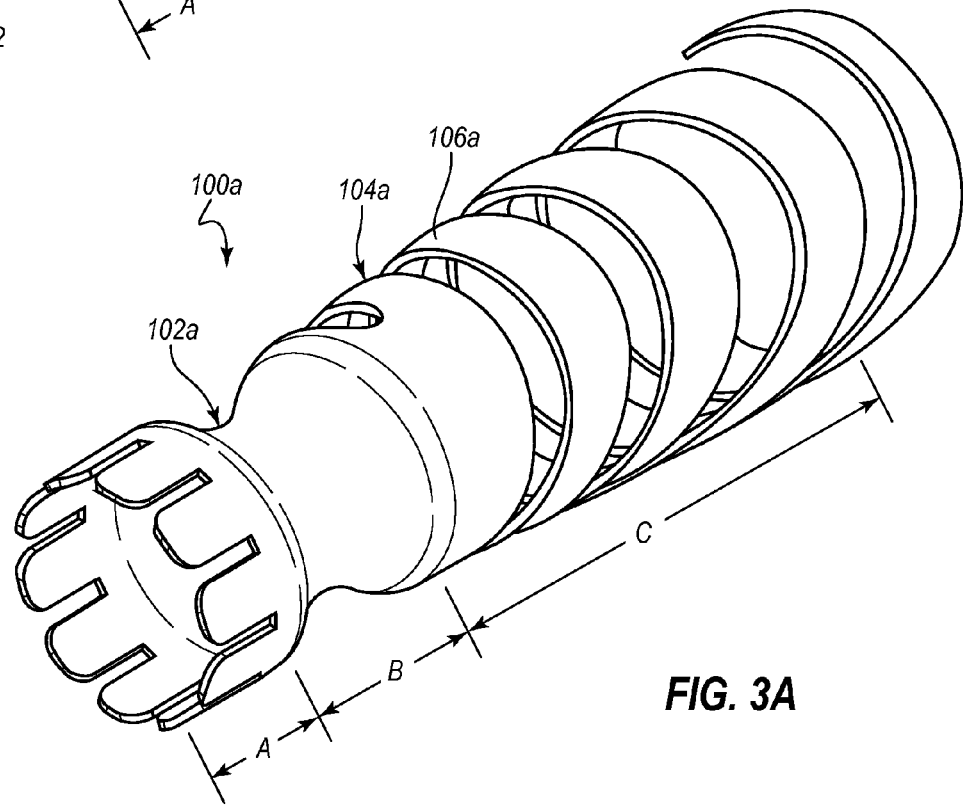

Having thus described the invention in general terms, reference will now be made to the accompanying drawings, which are not necessarily drawn to scale, and wherein:

FIG. 1 is a perspective view of a stent according to one embodiment of the present invention;

FIG. 2 is a cross-sectional view of a lumen of the duodenum illustrating the stent shown in FIG. 1 positioned proximate to a stricture;

FIG. 3 is a perspective view of a stent according to another embodiment of the present invention;

FIG. 3A is a perspective view of a stent according to another embodiment of the present invention;

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIG. 1, a duodenum stent 10 is shown. The stent 10 generally includes a stent region 12 (depicted generally as region "B") and a pair of transition regions 14 (depicted generally as regions "A" and "C") positioned on opposed ends of the stent region. The stent region 12 includes a smaller diameter portion than that of each of the transition regions 14. Generally, the stent region 12 is positioned within the lumen 11 adjacent to a stricture 15, while each of the transition regions 14 are positioned proximally and distally of the stricture, as shown in FIG. 2. The stricture can occur as the result of splicing operation, as discussed above, which attaches together two cut ends of the duodenum. A ring of scar tissue often forms, and this ring protrudes into the duodenum causing the stricture. Thus, the stent region 12 performs typical stenting functions proximate to the stricture, while the transition regions 14 are configured to reduce the incidence of migration and misalignment of the duodenum stent 10. Advantageously, a recessed and concave portion of the stent region 12 receives the stricture and anchors the stent to prevent migration axially along the duodenum. Thus, the stent according to the present invention can use the abnormality of the stricture to help position and restrain the stent.

Thus, the duodenum stent 10 is capable of being deployed within a lumen of the duodenum. However, although reference is made herein to a biliary stent 10, it is understood that the stent is applicable to a wide range of stenting applications. For example, the stent 10 could be used for stenting lumens of the esophagus, vascular lumens, or lumens of the biliary tract. Furthermore, although reference is made herein to a "stricture," it is understood that the biliary stent 10 may be used to treat strictures, lesions, tumors, or other complications where the lumen passageway has been significantly reduced.

The stent region 12 may include a scaffolding of struts. The struts generally include a plurality of interconnected legs and connectors, as known to those skilled in the art. The stent region 12 includes a series of legs arranged circumferentially about the stent, as well as arranged in a series of rows along the longitudinal axis of the stent, while a plurality of connectors are arranged parallel to the longitudinal axis of the stent to connect the rows together.

The stent region 12 is preferably formed from a material such as Ni, C, Co, Cu, Cr, H, Fe, Nb, O, SS, Ti and composites, alloys and combinations thereof (e.g., Nitinol), but could also be formed of polymeric materials. The material is generally formed into a tube from which the stent is etched or laser cut and is formed on a suitable shaping device to give the stent the desired external geometry. The stent region 12 is formed of a memory material that facilitates flexibility of the stent region such that the stent region may be deformed and return to its original shape. This flexibility allows the stent to be compressed radially for insertion into a stent delivery device, as discussed below, so as to self-expand when released into the lumen. However, the stent region 12 is not necessarily formed from self-expanding or shape-changing material, and the diameter of the stent region may remain the same before and after the transition regions 14 compressed to be inserted into a delivery device.

The stent region 12 is generally cylindrical, having openings at the proximal and distal ends. As illustrated in FIG. 1, the diameter of the proximal and distal ends of the stent region 12 is larger than the diameter of a medial portion 13 of the stent extending therebetween so as to define a concave portion for receiving the stricture and anchoring the stent relative to the stricture. In the event the stent region 12 is to be shaped to the dimensions of a particular lumen, optical photography and/or optical videography of the target lumen may be conducted prior to stent formation. The interstice geometry of the stent region 12 then can be etched and formed in accordance with the requirements of that target lumen and/or stricture. For example, if the topography of the lumen and/or stricture of a particular patient is captured optically and the appropriate dimension provided, a patient-specific prosthesis could be engineered. These techniques can be adapted to other non-vascular lumina but is very well suited for vascular applications where the specific topography of a patient's lumen is a function of a variety of factors such as genetics, lifestyle, etc.

It should be pointed out that, unlike the use of differing shape memory materials to change portions of a stent region 12, stent regions in accordance with the present invention can take on an infinite number of characteristic combinations of interstice geometry by changing angles, segment lengths, and segment thicknesses during the cutting and forming stages of stent engineering or during post-formation processing and polishing steps. Moreover, by modifying the geometry of the connectors, additional functionality may be achieved. Furthermore, the stent region 12 may be coated or covered in alternative aspects of the present invention and as known to those skilled in the art.

Any number of configurations of stent regions 12 could be incorporated and still be within the present scope of the invention. An exemplary embodiment of the interstice geometry of a stent region 12 and methods of manufacturing that may be used for the stent are disclosed in U.S. Patent Application Publication No. 20040127973, entitled "Removable Biliary Stent," which is assigned to the present assignee and is incorporated herein by reference. Thus, the interstice geometry of the stent region 12 should not be limited to that described herein, as any number of configurations of interstice geometry could be employed with the present invention to achieve various degrees of rigidity and functionality.

Each of the transition regions 14 extends from respective proximal and distal ends of the stent region 12. The transition regions 14 generally have a larger diameter than at least the medial portion 13 of the stent region 12. The transition regions 14 include an aperture extending therethrough that is substantially collinear with an aperture extending through the stent region 12 such that the duodenum stent 10 is generally tubular for allowing fluids to pass therethrough.

Each of the transition regions 14 depicted in FIG. 1 includes a portion that is configured in a helix having several turns 16. Each of the turns 16 extends radially from a tubular portion 20 of each transition region 14. The tubular portion 20 of each transition region 14 extends adjacent to the proximal and distal ends of the stent region 12. The tubular portions 20 are substantially tubular and could include additional turns 16, be solid as shown, or include scaffolding as described above with respect to the stent region 20. Thus the tubular portions 20 and stent region 12 may collectively include scaffolding substantially between the turns 16 of each helix. Similarly, the turns 16 of the helix could include scaffolding if desired, such that the entire duodenum stent 10 includes scaffolding.

Each turn 16 is separated by a gap 18, and the turns extend angularly with respect to one another and, thus, include a pitch. The gaps 18 may be the same width or vary in width between each turn 16, and the width and diameter or each turn may also vary between adjacent turns. For example, the turns 16 may decrease in width further away from the stent region 12 such that the last turn furthest from the stent region is the narrowest in width. Also, the turns 16 could increase in diameter such that the transition regions 14 flare outwardly from the proximal and distal ends of the stent region 12. Alternatively, the gaps 18 could increase in width further outwardly from the stent region 12. It is also understood that there could be no gaps 18 between turns 16 if desired, and that the gaps could vary as the transition regions 14 expand and contract.

To add support to the transition regions 14, connectors 22 may be positioned between adjacent turns 16 and across a gap 18. Thus, the gaps 18 could be non-continuous about each turn 16 such that the connectors 22 extend across the gaps at various locations to increase the rigidity of the transition regions 14. Furthermore, the duodenum stent 10 may include radiopaque markers 24 (e.g., platinum iridium), as known to those skilled in art, at various locations to aid in positioning the stent within the lumen.

FIG. 1 shows a first transition region (generally depicted as region "C") 14 that includes approximately five turns 16, while a second transition region (generally depicted as region "A") includes approximately three turns. However, it is understood that the transition regions 14 may include any number of turns 16 to vary the length or flexibility of the duodenum stent 10. Accordingly, although the first transition region 14 is shown as being longer than the second transition region and includes a greater number of turns 16, it is understood that the transition regions could be the same length, or the second transition region could be longer than the first transition region. Moreover, each of the transition regions 14 may be any number of sizes and configurations and still be within the scope of the present invention. Thus, although each of the transition regions 14 typically has the same diameter, the transition regions could be different diameters in variations of the duodenum stent 10. The outer diameter of the transition region 14 could be approximately 25 mm and the medial portion 13 of the stent region 12 about 5-10 mm smaller in diameter than the transition regions.

The turns 16 of each helix are typically formed from a flat piece of material. Therefore, each of the turns 16 includes a substantially rectangular cross section. Once the appropriate length and number of turns of a transition region 14 has been determined, a continuous strip of material is wound around a mandrel or shaping device to form the helix. The transition region 14 could also be formed from a tubular member such that the gaps 18 are cut out of the tube to define the turns 16. In addition, the stent 12 and transition 14 regions could be formed from the same tubular member. The transition regions 14 are typically formed of a flexible memory material, which could be the same or similar to that of the stent region 12. Thus, the transition regions 14 are capable of recovering to an original shape after being deformed, and the helices are capable of closely mimicking the lumen as the lumen changes position and shape. The transition regions 14 could also be a different material than that of the stent region 12 such as a more flexible material. In such a case, the transition regions 14 are attached to the stent region 12 using connectors. The connectors could be integrated or formed separately from the stent 12 and transition 14 regions. In addition, the connectors could be flexible and fabricated with a different material than the stent 12 and transition 14 regions for imparting various amounts of flexibility along the length of the stent 10.

FIG. 3 illustrates an additional embodiment of the present invention. As described above, the duodenum stent 100 includes a stent region 102 (generally shown as region "B") and a pair of transition regions 104 (generally shown as regions "A" and "C") extending outwardly from the proximal and distal ends of the stent region. As also described above, a first transition region 104 includes a helix having a series of turns 106 separated by gaps 108. FIG. 3A illustrates an additional embodiment of a duodenum stent 100a with a first transition region 104a including a helix having a series of turns 106a with different widths and each of the turns 106a of the helix increases in diameter as the turns 106a extend further away from the stent region 102a.

FIG. 3 demonstrates that the second transition region 104 includes a plurality of leg members 110 separated by gaps 112. The leg members 110 are arranged circumferentially about an end of the stent region 102. The leg members 110 also extend axially and substantially parallel to the longitudinal axis of the aperture extending through each of the stent 102 and transition 104 regions. In addition, the leg members 110 are generally the same length and are generally rectangular with the major axis of the leg members extending axially. The leg members 110 also include a substantially rectangular cross section. As described above, the leg members could include connectors 114 and markers 116 if desired.

Figure 4:
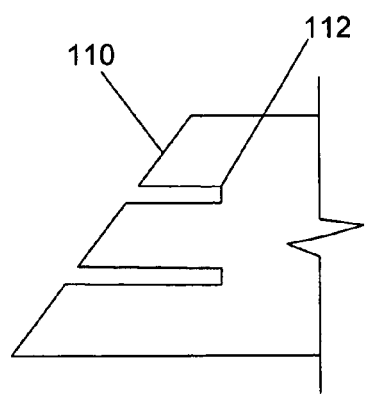
Figure 5:
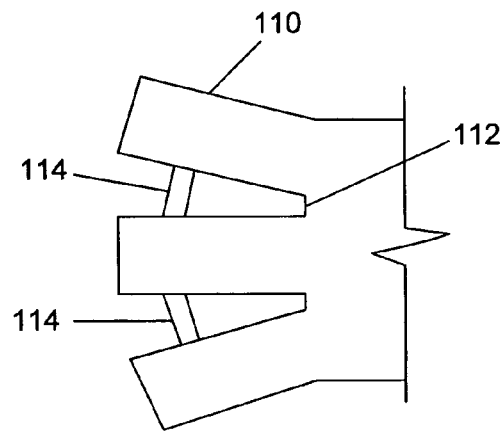
Figure 6:
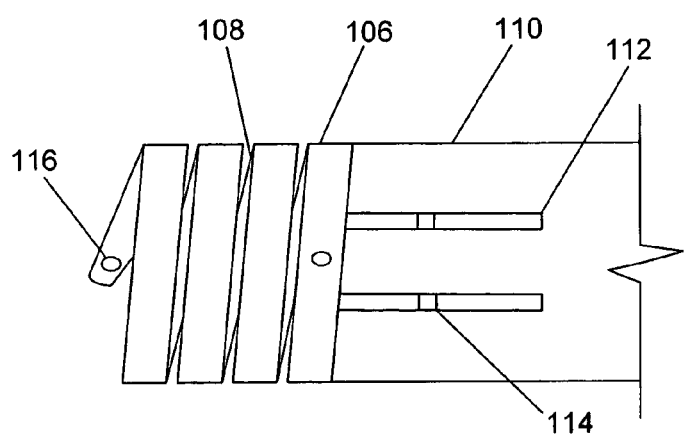

However, the leg members 110 should not be limited to that shown in FIG. 3, as the leg members could be various sizes and configurations in variations of the present invention. For example, each of the leg members 110 could be various lengths, and the gaps 112 could be a range of widths. Similarly, although FIG. 3 shows ten leg members 110, it is understood that there could be any number of leg members in additional aspects of the present invention. In one embodiment illustrated in FIG. 4, the length of each of the leg members 110 is varied circumferentially such that the leg members define an angular opening. In addition, the leg members 110 may be non-rectangular such that the leg members could be, for instance, triangular with the apex of the leg members extending outwardly and axially from the stent region 102. The leg members 110 may also flare outwardly at a predetermined angle from the stent region 102, as shown in FIG. 5, or the leg members could be configured as a balloon such that the stent 100 is arranged in a dog-bone like configuration. Moreover, a helix, as described above, may extend from one or more leg members 110 and extend outwardly and circumferentially as depicted in FIG. 6.

The leg members 110 may be formed separately from the stent region 102 and attached using various techniques, such as welding, gluing, etc. For example, the leg members 110 could be formed or cut from a flat piece of material to resemble a "fence" and then wrapped circumferentially about a mandrel and attached to an end of the stent region 102. Alternatively, the leg members 110 could be formed from a tubular blank, where the gaps 112 are cut or etched out of the tubular blank. In one embodiment of the present invention, the stent region 102 and leg members 110 could be integrally formed from the same tubular member. As described above with respect to the transition regions 14 and 104 defining a helix, the leg members 110 are preferably formed of a flexible memory material, which is the same or similar to that of the stent region 102. Thus, the leg members 110 are at least as flexible as the stent region 102 and are advantageously more flexible.

The duodenum stents 10 and 100 are deployed within a lumen of the duodenum using techniques known to those skilled in the art. For example, the biliary stent is typically contracted to a smaller first diameter from a relaxed position. Once contracted, the biliary stent is positioned within a delivery device, such as catheter or tube that may be inserted within the lumen. For example, an endoscope could be used to position and deploy the duodenum stent within the lumen. An example of an endoscope suitable for implanting the duodenum stent is disclosed in U.S. Patent Application Publication No. 20040193243, entitled "Medical Appliance Optical Delivery and Deployment Apparatus and Method," which is assigned to the present assignee and incorporated herein by reference. Similarly, techniques and devices known to those skilled in the art used to locate, contract, and/or remove the duodenum stent from the lumen may be employed with the present invention.

The duodenum stent is typically introduced orally with the endoscope, through the lumen, and proximate to a stricture. The smaller diameter portion of the stent region 12 102 is positioned proximate to the stricture such that when the duodenum stent is deployed from the catheter or tube, the stent region, if formed from an expansible material, can expand to receive the stricture and even expand the diameter of the stricture. For example, the stent region could open up the stricture approximately 10-25 mm. Similarly, the transition regions 14 or 104 will be positioned proximally and distally of the stricture and when deployed from the endoscope, will expand to contact the healthy tissue of the lumen. Because the larger diameter transition regions are positioned on opposed sides of the smaller diameter stricture and stent region, the duodenum stent is less likely to migrate. In addition, the scar tissue that formed the stricture aids in securing the duodenum stent 10 in position. The more flexible transition regions are capable of dynamically expanding and retracting to closely mimic the motion of the lumen, which is beneficial for lumens such as the duodenum or esophagus where the lumen frequently changes size and position.

The present invention includes several advantages. The duodenum stent is capable of opening up a stricture within a lumen to allow for normal fluid flow (e.g., bile) within the duodenum. Because the embodiments of the duodenum stent include a stent region that is smaller in diameter than the transition regions, the stent region may be positioned proximate to the stricture such that the stricture aids in securing the stent within the lumen. The larger diameter portions of the transition regions are flexible and formed of memory material that is capable of adapting to changes in position and size of the lumen. Thus, the stent and transition regions cooperate to decrease the incidence of stent migration. Moreover, because the duodenum stent may include various configurations of stent and transition regions, the duodenum stent is capable of being customized for a particular lumen or patient.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A flexible stent for positioning within a body lumen, the stent comprising:
   a stent region having a proximal end and a distal end and a first aperture defined therethrough;
   a first transition region extending outwardly from the proximal end of the stent region and at least a portion of the first transition region configured in a helix comprising a plurality of turns, the first transition region having a larger diameter than at least a portion of the stent region, the helix defining a second aperture therethrough; and
   a second transition region extending outwardly from the distal end of the stent region, the second transition region having a larger diameter than at least a portion of the stent region and having a third aperture defined therethrough,
   wherein the second transition region comprises a plurality of leg members extending axially from the distal end of the stent region and each of the leg members extends from near the distal end of the stent region to a distal end of the second transition region, wherein each of the leg members are a different length,
   wherein at least one of the first transition region and the second transition region includes a gap extending from near the stent region to a free end of a respective transition region such that the gap does not extend within the stent region, and wherein each of the first and second transition regions are capable of expanding from a first diameter prior to being deployed into the lumen to a larger second diameter after being deployed into the lumen, wherein each of the first, second, and third apertures are collinear.

2. The stent according to claim 1, wherein the proximal and distal ends of the stent region flare outwardly from a medial portion of the stent region such that a diameter of each of the first and second transition regions is larger than the medial portion.

3. The stent according to claim 1, wherein each of the turns of the helix comprises a different width.

4. The stent according to claim 1, wherein each of the turns comprises a rectangular cross section.

5. The stent according to claim 1, wherein the helix comprises at least three turns.

6. The stent according to claim 1, wherein the first transition region includes a turn-gap extending from the proximal end of the stent region to a free end of the first transition region such that each of the turns is separated by the turn-gap, and wherein a width of the turn-gap is smaller than a width of each turn.

7. The stent according to claim 6, further comprising a plurality of connectors, wherein each connector extends across each turn-gap and between respective turns of the helix.

8. The stent according to claim 1, wherein each of the turns of the helix increases in diameter as the turns extend further away from the stent region.

9. The stent according to claim 1, wherein adjacent leg members are separated by a leg-gap, wherein each leg-gap extends from the distal end of the stent region to a free end of the second transition region, and wherein a width of each leg-gap is smaller than a width of each leg member.

10. The stent according to claim 1, wherein each of the leg members comprises a rectangular cross section.

11. The stent according to claim 1, wherein each of the leg members are parallel to one another and to each of the first, second, and third apertures.

12. The stent according to claim 1, wherein each of the leg members angle outwardly from the distal end of the stent region.

13. The stent according to claim 1, wherein the second transition region further comprises a second helix extending from at least one of the leg members.

14. The stent according to claim 1, wherein the leg members are configured to define an angled opening.

15. The stent according to claim 1, wherein the first transition region is longer than the second transition region.

16. The stent according to claim 1, wherein each of the transition regions comprises a more flexible material than the stent region.

17. The stent according to claim 1, wherein each of the first and second transition regions has the same diameter between its respective proximal and distal ends.

18. A method for deploying a stent within a body lumen comprising:
providing a stent comprising
a stent region having a proximal end and a distal end, the stent region defining a first aperture therethrough;
a first transition region extending from the proximal end of the stent region, wherein at least a portion of the first transition region is configured in a helix comprising a plurality of turns, the helix defining a second aperture,
a second transition region extending from the distal end of the stent region, the second transition region defining a third aperture, wherein the second transition region comprises a plurality of leg members extending axially from the distal end of the stent region and each of the leg members extending from near the distal end of the stent region to a distal end of the second transition region, wherein adjacent leg members are separated by a leg-gap, each leg-gap extending from the distal end of the stent region to the distal end of the second transition region, and a width of each leg-gap being smaller than a width of each leg member,
wherein each of the first, second, and third apertures are collinear;
compressing the stent to a diameter smaller than that of the lumen;
positioning the stent in a predetermined position within the lumen; and
deploying the stent within the lumen such that the stent region expands to conform to a stricture and each of the transition regions expands to conform to the lumen proximally and distally of the stricture.

19. The method according to claim 18, wherein positioning comprises positioning the stent within the lumen with an endoscope.

20. The method according to claim 18, wherein the first transition region includes a turn-gap extending from the proximal end of the stent region to a free end of the first transition region such that each of the turns is separated by the turn-gap, and wherein a width of the turn-gap is smaller than a width of each turn.

21. A flexible stent for positioning within a body lumen, the stent comprising:
a stent region having a proximal end and a distal end and a first aperture defined therethrough;
a first transition region configured as a helix comprising a plurality of turns, the helix defining a second aperture therethrough, the first transition region extending outwardly from the proximal end of the stent region; and
a second transition region defining a third aperture therethrough, the second transition region extending outwardly from the distal end of the stent region, wherein the second transition region comprises a plurality of leg members extending axially from the distal end of the stent region, adjacent leg members being separated by a leg-gap that extends from a distal end of the stent region to a distal end of the second transition region, and a width of each leg-gap being smaller than a width of each leg member
wherein each of the first, second, and third apertures are collinear.

22. The stent according to claim 21, wherein each of the first and second transition regions has a larger diameter than at least a portion of the stent region.

23. The stent according to claim 21, wherein each of the first and second transition regions has the same diameter between its respective proximal and distal ends.

24. A flexible stent for positioning within a body lumen, comprising:
a stent region having a proximal end and a distal end and a first aperture defined therethrough;
a first transition region extending outwardly from the proximal end of the stent region and at least a portion of the first transition region configured in a helix comprising a plurality of turns, the first transition region having a larger diameter than at least a portion of the stent region, the helix defining a second aperture therethrough; and a second transition region extending outwardly from the distal end of the stent region, the second transition region having a larger diameter than at least a portion of the stent region and having a third aperture defined therethrough, wherein the second transition region comprises a plurality of leg members extending axially from the distal end of the stent region, wherein each of the leg members extends from near the distal end of the stent region to a distal end of the second transition region, and wherein adjacent leg members are separated by a leg-gap, wherein each leg-gap extends from the distal end of the stent region to the distal end of the second transition region, and wherein a width of each leg-gap is smaller than a width of each leg member, wherein each of the first and second transition regions are capable of expanding from a first diameter prior to being deployed into the lumen to a larger second diameter after being deployed into the lumen; and wherein each of the first, second, and third apertures are collinear.

25. The stent according to claim 24, wherein the proximal and distal ends of the stent region flare outwardly from a medial portion of the stent region such that a diameter of each of the first and second transition regions is larger than the medial portion.

26. The stent according to claim 24, wherein each of the turns of the helix comprises a different width.

27. The stent according to claim 24, wherein each of the turns comprises a rectangular cross section.

28. The stent according to claim 24, wherein the helix comprises at least three turns.

29. The stent according to claim 24, wherein the first transition region includes a turn-gap extending from the proximal end of the stent region to a free end of the first transition region such that each of the turns is separated by the turn-gap, and wherein a width of the turn-gap is smaller than a width of each turn.

30. The stent according to claim 29, further comprising a plurality of connectors, wherein each connector extends across each gap and between respective turns of the helix.

31. The stent according to claim 24, wherein each of the turns of the helix increases in diameter as the turns extend further away from the stent region.

32. The stent according to claim 24, wherein each of the leg members comprises a rectangular cross section.

33. The stent according to claim 24, wherein each of the leg members are parallel to one another and to each of the first, second, and third apertures.

34. The stent according to claim 24, wherein each of leg members angle outwardly from the distal end of the stent region.

35. The stent according to claim 24, wherein the second transition region further comprises a second helix extending from at least one of the leg members.

36. The stent according to claim 24, wherein each of the leg members are a different length.

37. The stent according to claim 24, wherein the leg members are configured to define an angled opening.

38. The stent according to claim 24, wherein the first transition region is longer than the second transition region.

39. The stent according to claim 24, wherein each of the transition regions comprises a more flexible material than the stent region.

40. The stent according to claim 24, wherein each of the first and second transition regions has the same diameter between its respective proximal and distal ends.

* * * * *

UNITED STATES PATENT AND TRADEMARK OFFICE
CERTIFICATE OF CORRECTION

| | | |
|---|---|---|
| PATENT NO. | : 8,323,350 B2 | Page 1 of 1 |
| APPLICATION NO. | : 11/400630 | |
| DATED | : December 4, 2012 | |
| INVENTOR(S) | : Nissl | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 539 days.

Signed and Sealed this
Eleventh Day of November, 2014

Michelle K. Lee
*Deputy Director of the United States Patent and Trademark Office*